US011357571B2

United States Patent
Yoneyama et al.

(10) Patent No.: US 11,357,571 B2
(45) Date of Patent: Jun. 14, 2022

(54) STENT LENGTH ESTIMATION DEVICE, STENT LENGTH ESTIMATION PROGRAM, AND METHOD OF ESTIMATING LENGTH OF STENT

(71) Applicant: PENTAS Inc., Tokyo (JP)

(72) Inventors: Shigeru Yoneyama, Tokyo (JP); Hiroyuki Takao, Tokyo (JP); Takashi Suzuki, Tokyo (JP)

(73) Assignee: PENTAS Inc., Tokyo (JP)

( * ) Notice: Subject to any disclaimer, the term of this patent is extended or adjusted under 35 U.S.C. 154(b) by 644 days.

(21) Appl. No.: 16/075,277

(22) PCT Filed: Feb. 9, 2017

(86) PCT No.: PCT/JP2017/004699
§ 371 (c)(1),
(2) Date: Aug. 3, 2018

(87) PCT Pub. No.: WO2017/141803
PCT Pub. Date: Aug. 24, 2017

(65) Prior Publication Data
US 2019/0038358 A1    Feb. 7, 2019

(30) Foreign Application Priority Data

Feb. 16, 2016 (JP) .............................. JP2016-026784

(51) Int. Cl.
*A61B 34/10* (2016.01)
*A61F 2/88* (2006.01)
(Continued)

(52) U.S. Cl.
CPC ................ *A61B 34/10* (2016.02); *A61F 2/88* (2013.01); *A61F 2/90* (2013.01); *A61B 6/032* (2013.01);
(Continued)

(58) Field of Classification Search
None
See application file for complete search history.

(56) References Cited

U.S. PATENT DOCUMENTS 6,782,284 B1    8/2004  Subramanyan
8,548,778 B1   10/2013  Hart
(Continued)

FOREIGN PATENT DOCUMENTS

JP    2001079097 A    3/2001
JP    2005510280 A    4/2005
(Continued)

OTHER PUBLICATIONS

Ignacio Larrabide et al., "Fast virtual deployment of self-expandable stents: method and in vitro evaluation for intracranial aneurysmal stenting," 2012, Medical Image Analysis, vol. 16, pp. 721-730 (Year: 2012).*

(Continued)

*Primary Examiner* — Brian S Cook
*Assistant Examiner* — Russ Guill
(74) *Attorney, Agent, or Firm* — Rankin, Hill & Clark LLP

(57) ABSTRACT

To estimate the length of a stent implanted in a blood vessel after implantation of the stent. A stent length estimation device 100 includes an implantation start position specifying means for receiving, from a user, a designation of an implantation start position of an aneurysm treatment stent which is formed by helicoidally braiding a plurality of metal wires and specifying the implantation start position of the stent on a three-dimensional blood vessel image which represents a three-dimensional shape of the blood vessel, an implantation direction specifying means for receiving a designation of an implantation direction of the stent from the user and specifying the implantation direction of the stent on (Continued)

the three-dimensional blood vessel image, a stent specification specifying means for specifying a diameter of the stent after expanded, a length of the stent after expanded, the number of wires of the stent, and a pitch length of the wires of the stent after expanded as a specification of the stent, and an implanted stent length calculating means for calculating a length of the stent which is implanted and expanded along with a blood vessel diameter on the basis of the specification of the stent specified by the stent specification specifying means and the blood vessel diameter of the blood vessel in the implantation direction specified by the implantation direction specifying means from the implantation start position specified by the implantation start position specifying means.

9 Claims, 7 Drawing Sheets

(51) Int. Cl.
*A61F 2/90* (2013.01)
*A61F 2/82* (2013.01)
*A61B 6/03* (2006.01)
*A61B 6/12* (2006.01)
*A61B 90/00* (2016.01)

(52) U.S. Cl.
CPC ........... *A61B 6/12* (2013.01); *A61B 2034/104* (2016.02); *A61B 2090/374* (2016.02); *A61B 2090/3762* (2016.02); *A61F 2002/823* (2013.01); *A61F 2240/002* (2013.01); *A61F 2240/005* (2013.01); *A61F 2240/008* (2013.01)

(56) References Cited

U.S. PATENT DOCUMENTS

| | | | |
|---|---|---|---|
| 9,028,541 B2 | 5/2015 | Abunassar | |
| 2002/0143390 A1* | 10/2002 | Ishii | A61F 2/91 623/1.15 |
| 2003/0105517 A1* | 6/2003 | White | A61F 2/91 623/1.17 |
| 2003/0191516 A1 | 10/2003 | Weldon | |
| 2005/0148902 A1 | 7/2005 | Minar | |
| 2005/0246010 A1 | 11/2005 | Alexander | |
| 2006/0241469 A1* | 10/2006 | Rold | A61B 8/463 600/459 |
| 2007/0135707 A1* | 6/2007 | Redel | A61B 6/504 600/424 |
| 2010/0086190 A1 | 4/2010 | Sakaguchi | |
| 2012/0310611 A1* | 12/2012 | Sadasivan | A61F 2/90 703/6 |
| 2012/0323547 A1* | 12/2012 | Baloch | G16H 50/50 703/11 |
| 2013/0018665 A1* | 1/2013 | Jung | G06Q 10/08 705/2 |
| 2013/0231548 A1 | 9/2013 | Brown | |
| 2014/0270436 A1 | 9/2014 | Dascal | |
| 2015/0335304 A1 | 11/2015 | Lavi | |
| 2015/0370995 A1 | 12/2015 | Wakai | |
| 2015/0374483 A1* | 12/2015 | Janardhan | A61B 17/221 606/200 |
| 2016/0157808 A1* | 6/2016 | Merritt | A61B 5/0035 600/427 |
| 2016/0217375 A1* | 7/2016 | Choi | G16H 30/40 |
| 2016/0232659 A1* | 8/2016 | Larrabide | G06T 7/0012 |

FOREIGN PATENT DOCUMENTS

| | | |
|---|---|---|
| JP | 2005521514 A | 7/2005 |
| JP | 2006508744 A | 3/2006 |
| JP | 2007535364 A | 12/2007 |
| JP | 2008531200 A | 8/2008 |
| JP | 2010110619 A | 5/2010 |
| JP | 2011045449 A | 3/2011 |
| JP | 2014046211 A | 3/2014 |
| JP | 2014188323 A | 10/2014 |
| JP | 2015134196 A | 7/2015 |
| JP | 2015522376 A | 8/2015 |
| WO | 2014111927 A1 | 7/2014 |

OTHER PUBLICATIONS

"Command Reference," 2010, Autodesk, Inc., six pages (Year: 2010).*
"Inventor Forum," 2015, https://forums.autodesk.com/t5/inventor-forum/coronary-stent/td-p/5830610, 4 pages (Year: 2015).*
Michael R. Jedwab et al., "A study of the geometrical and mechanical properties of a self-expanding metallic stent—theory and experiment," 1993, Journal of Applied Biomaterials, vol. 4, pp. 77-85 (Year: 1993).*
"Inventor Forum," 2009, https://forums.autodesk.com/t5/inventor-forum/spiral-length-formula/td-p/2575288, 3 pages; (Year: 2009).*
Chenhaoxu, "Design and simulation of a magnesium based biodegradable stent for hemodialysis application," 2015, University of Cincinnati, 109 pages (Year: 2015).*
Fernandez, Hector et al., "Computation of the change in length of a braided device when deployed in realistic vessel models," International Journal of Computer Assisted Radiology and Surgery, Jun. 2015, p. 1659-1665, vol. 10 No.10, Springer Publishing Company, U.S.A.; Cited in ISR.
International Search Report dated May 9, 2017 filed in PCT/JP2017/004699.

* cited by examiner

STENT LENGTH ESTIMATION DEVICE, STENT LENGTH ESTIMATION PROGRAM, AND METHOD OF ESTIMATING LENGTH OF STENT

TECHNICAL FIELD

The present invention relates to a stent length estimation device, a stent length estimation program, and a method of estimating a length of the stent.

BACKGROUND ART

There is known the following image processing device. In the image processing device, a positional relation between a stent implanted in a blood vessel and the blood vessel can be ascertained (see Patent Literature 1).

CITATION LIST

Patent Literature
Patent Literature 1: JP 2011-45449 A

SUMMARY OF INVENTION

Technical Problem

In recent years, a cerebral aneurysm treatment is performed using a stent (for example, a flow diverter stent) formed by helicoidally braiding a plurality of metal wires. In the use of the stent formed by helicoidally braiding the metal wires such as the flow diverter stent, a length of the stent in a case where the stent is implanted in the blood vessel is desirably estimated in consideration of a phenomenon such as a foreshortening in which the length of the stent is shortened in a procedure that the stent is released from a catheter into the blood vessel so as to determine an implantation range of the stent. However, the related art fails to review any technology that ascertains a change in length of the stent in advance when the stent is implanted in the blood vessel of a patient in consideration of the foreshortening.

Solution to Problem

According to a first aspect of the invention, the stent length estimation device includes an implantation start position specifying means for receiving, from a user, a designation of an implantation start position of an aneurysm treatment stent which is formed by helicoidally braiding a plurality of metal wires, and specifying the implantation start position of the stent on a three-dimensional blood vessel image which represents a three-dimensional shape of a blood vessel, an implantation direction specifying means for receiving a designation of an implantation direction of the stent from the user, and specifying the implantation direction of the stent on the three-dimensional blood vessel image, a stent specification specifying means for specifying a diameter of the stent after expanded, a length of the stent after expanded, the number of wires of the stent, and a pitch length of the wires of the stent after expanded as a specification of the stent, and an implanted stent length calculating means for calculating a length of the stent which is implanted and expanded along with a blood vessel diameter on the basis of the specification of the stent specified by the stent specification specifying means and the blood vessel diameter of the blood vessel in the implantation direction specified by the implantation direction specifying means from the implantation start position specified by the implantation start position specifying means.

According to a second aspect of the invention, the stent length estimation device of the first aspect further includes a display means for displaying information indicating the implantation start position of the stent and information indicating an implantation end position in the three-dimensional blood vessel image on the basis of the implantation start position of the stent which is specified by the implantation start position specifying means, the implantation direction of the stent which is specified by the implantation direction specifying means, and an implanted stent length which is calculated by the implanted stent length calculating means.

According to a third aspect of the invention, the implanted stent length calculating means in the stent length estimation device of the first or second aspect divides the blood vessel into fine sections on the three-dimensional blood vessel image, calculates a length of the implanted stent for every fine section, and calculates the implanted stent length by summing up the lengths.

According to a fourth aspect of the invention, a stent length estimation program causes a computer to perform an implantation start position specifying procedure for receiving, from a user, a designation of an implantation start position of an aneurysm treatment stent which is formed by helicoidally braiding a plurality of metal wires and specifying the implantation start position of the stent on a three-dimensional blood vessel image which represents a three-dimensional shape of a blood vessel, an implantation direction specifying procedure for receiving, from the user, a designation of the implantation direction of the stent and specifying the implantation direction of the stent on the three-dimensional blood vessel image, a stent specification specifying procedure for specifying a diameter of the stent after expanded, a length of the stent after expanded, the number of wires of the stent, and a pitch length of the wires of the stent after expanded as a specification of the stent, and an implanted stent length calculating procedure for calculating a length of the stent which is implanted and expanded along with the blood vessel diameter on the basis of the specification of the stent which is specified by the stent specification specifying procedure and a blood vessel diameter of the blood vessel in the implantation direction which is specified by the implantation direction specifying procedure from the implantation position start position specified by the implantation start position specifying procedure.

According to a fifth aspect of the invention, the stent length estimation program of the fourth aspect further includes a display procedure for displaying information indicating the implantation start position of the stent and information indicating an implantation end position in the three-dimensional blood vessel image on the basis of the implantation start position of the stent which is specified by the implantation start position specifying procedure, the implantation direction of the stent which is specified by the implantation direction specifying procedure, and the implanted stent length which is calculated by the implanted stent length calculating procedure.

According to a sixth aspect of the invention, in the stent length estimation program of the fourth or fifth aspect, the implanted stent length calculating procedure divides the blood vessel into fine sections on the three-dimensional blood vessel image, calculates a length of the implanted stent for every fine section, and calculates the implanted stent length by summing up the lengths.

According to a seventh aspect of the invention, a method of estimating a length of a stent includes receiving, by an implantation start position specifying means from a user, a designation of an implantation start position of an aneurysm treatment stent which is formed by helicoidally braiding a plurality of metal wires and specifying the implantation start position of the stent on a three-dimensional blood vessel image which represents a three-dimensional shape of a blood vessel, receiving, by an implantation direction specifying means, a designation of the implantation direction of the stent from the user and specifying the implantation direction of the stent on the three-dimensional blood vessel image, specifying, by a stent specification specifying means, a diameter of the stent after expanded, a length of the stent after expanded, the number of wires of the stent, and a pitch length of the wires of the stent after expanded as a specification of the stent, and calculating, by an implanted stent length calculating means, a length of the stent which is implanted and expanded along with the blood vessel diameter on the basis of the specification of the stent which is specified by the stent specification specifying means and a blood vessel diameter of the blood vessel in the implantation direction which is specified by the implantation direction specifying means from the implantation start position specified by the implantation start position specifying means.

According to an eighth aspect of the invention, the method of estimating the length of the stent of the seventh aspect further includes displaying, by a display means, information indicating the implantation start position of the stent and information indicating an implantation end position in the three-dimensional blood vessel image on the basis of the implantation start position of the stent which is specified by the implantation start position specifying means, the implantation direction of the stent which is specified by the implantation direction specifying means, and the implanted stent length which is calculated by the implanted stent length calculating means.

According to a ninth aspect of the invention, in the method of estimating the length of the stent of the seventh or eighth aspect, the implanted stent length calculating means divides the blood vessel into fine sections on the three-dimensional blood vessel image, calculates a length of the stent after implanted for every fine section, and calculates the implanted stent length by summing up the lengths.

Advantageous Effects of Invention

According to the invention, a length of a stent which is implanted and expanded along with a blood vessel diameter can be calculated on the basis of a specification of the stent. Therefore, an operator can ascertain the length of the stent in advance when the stent is implanted in a blood vessel of a patient.

DESCRIPTION OF EMBODIMENTS

Figure 1:
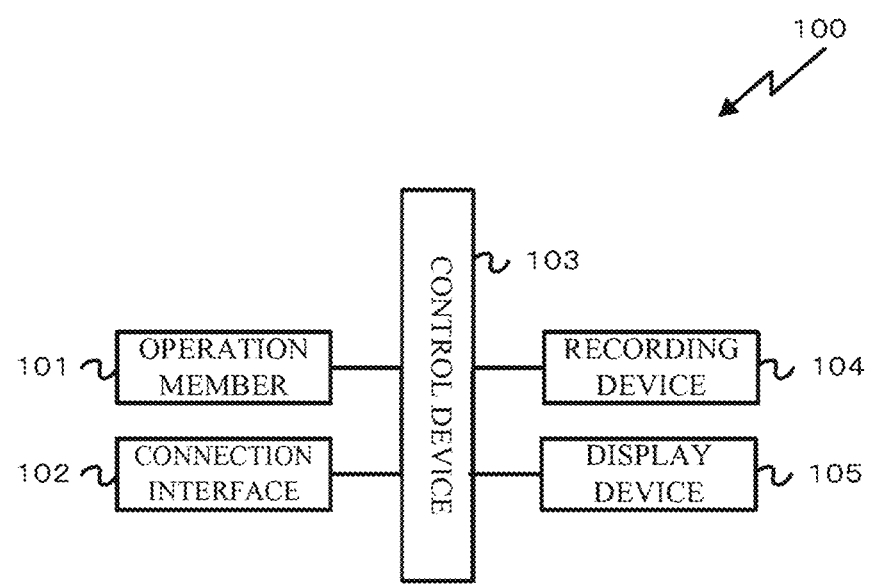
FIG. 1 is a block diagram illustrating a configuration of an embodiment of a stent length estimation device 100.

FIG. 1 is a block diagram illustrating a configuration of an embodiment of a stent length estimation device 100 according to this embodiment. As the stent length estimation device 100, for example, there is a server device or a personal computer where a program for executing a stent length estimation process (described below) is installed. FIG. 1 illustrates a configuration of an embodiment in a case where a personal computer is used as the stent length estimation device 100. The stent length estimation device 100 includes an operation member 101, a connection interface 102, a control device 103, a recording device 104, and a display device 105.

The operation member 101 includes various devices (for example, keyboard and mouse) operated by an operator of the stent length estimation device 100.

The connection interface 102 is an interface to connect the stent length estimation device 100 to the other devices or external devices such as a terminal. For example, the stent length estimation device 100 includes an interface for the connection of a communication line such as a LAN or the Internet, and an interface for the connection of an external memory medium.

The control device 103 is configured by a CPU, a memory, and other peripheral circuits, and controls the entire stent length estimation device 100. Further, the memory of the control device 103 is, for example, a volatile memory such as an SDRAM. The memory is used as a work memory to develop a program when the CPU executes a program, or a buffer memory to temporarily record data. For example, data read through the connection interface 102 is temporarily recorded in the buffer memory.

The recording device 104 is a memory medium to record various types of data which is accumulated in the stent length estimation device 100, and data of the program which is executed by the control device 103. As the recording device 104, for example, there are an HDD (Hard Disk Drive) and an SSD (Solid State Drive). Further, the data of the program to be recorded in the recording device 104 is provided as a recording medium (such as a CD-ROM and a DVD-ROM) recorded therein, or provided through a network. When the operator acquires the data of the program and installs the program in the recording device 104, the control device 103 executes the program.

The display device 105 is, for example, a liquid crystal monitor, and displays various types of display data which are output from the control device 103.

The stent length estimation device 100 in the embodiment performs a process of estimating a length of the stent when the stent is implanted in a blood vessel of a patient using three-dimensional data (hereinafter, referred to as "three-dimensional blood vessel data") of the blood vessel of the patient which is recorded in the recording device 104 in advance. In the embodiment, the three-dimensional blood vessel data obtained by capturing the blood vessel of a patient's brain in advance is recorded in the recording device 104. A process of estimating a length of the stent after implantation will be described on an assumption that the stent formed by helicoidally braiding a plurality of metal wires (for example, a flow diverter stent) is implanted in the blood vessel in order to treat a cerebral aneurysm which is one of cerebrovascular diseases. Further, in the embodiment, the denotation of the stent in the description means a stent formed by helicoidally braiding the plurality of metal wires like the flow diverter stent.

The three-dimensional blood vessel data recorded in the recording device 104 is assumed as being generated on the basis of image data captured at the time of examining a patient. A method of creating the three-dimensional blood vessel data is not particularly limited, and also may be created by the following method for example.

In general, if a photographic diagnosis of CTA (Computed Tomography Angiography), 3D-DSA (Three-Dimensional Digital Subtraction Angiography), and MRA (Magnetic Resonance Angiography) is performed at the time of treating a blood vessel disease such as a cerebral aneurysm, a captured image is stored as image data in conformity to a DICOM (Digital Imaging and Communication in Medicine) standard. In a photographic diagnosis, many layers of cross sections of a capturing target (for example, head) are captured. Therefore, by overlapping these tomographic images, three-dimensional image data of the capturing target can be created.

In the embodiment, the three-dimensional blood vessel data obtained by extracting only a blood vessel shape from the three-dimensional image data of the capturing target thus captured is recorded in the recording device 104. As a method of creating the three-dimensional blood vessel data obtained by extracting only the blood vessel shape from the three-dimensional image data of the capturing target, for example, the following method may be considered.

The capturing target is taken with different depths in the tomographic images according to materials. Therefore, when the image data of a region configured by pixels corresponding to the depth of the blood vessel is extracted from the three-dimensional image data of the capturing target, it is possible to create the three-dimensional blood vessel data obtained by extracting only the blood vessel shape. A concentration of color in the three-dimensional image data of the capturing target is determined by numerical information obtained at the time of capturing on the basis of a capturing principle of each modality. For example, in the case of CTA, an absorption degree of an X-ray, that is, an X-ray permeability is detected to perform the capturing. The X-ray permeability is expressed by a CT value (unit: HU) (for example, water is 0, and air is −1,000). The concentration of color is determined by a magnitude of the value. In other words, in the three-dimensional image data of the capturing target captured by CTA, numerical values from about −2,048 to +2,000 are already allocated to pixels according to the X-ray permeability.

For example, a numerical range corresponding to the depth of the blood vessel is set in advance. The three-dimensional image data of the capturing target is subjected to an image processing such that a pixel having the pixel value equal to or less than a lower limit value of the range is converted to white, and a pixel having the pixel value equal to or more than an upper limit value of the range is converted to black. In this way, a three-dimensional blood vessel image can be generated such that a pixel having the pixel value corresponding to the depth of the blood vessel is kept in the depth of color at the time of the capturing, and the other pixels are converted to white or black. The data of the generated three-dimensional blood vessel image is recorded in the recording device 104 as the three-dimensional blood vessel data. Herein, a threshold of the pixel value to extract the blood vessel region differs per person. Therefore, it is desirable that the threshold be set to be suitable to a patient at every processing.

In the embodiment, the control device 103 reads out the three-dimensional blood vessel data from the recording device 104 on the basis of a user's command and displays the data in the display device 105. With this configuration, a user of the stent length estimation device 100 such as a doctor can confirm the three-dimensional blood vessel image of the patient. Further, the three-dimensional blood vessel data is recorded for each patient. The operator can select a subject patient to command display of the three-dimensional blood vessel image.

When using the stent formed by helicoidally braiding the plurality of metal wires according to the embodiment, there may occur a phenomenon called the foreshortening in which the length of the stent is shortened during a procedure of releasing the stent from a catheter into the blood vessel. Therefore, an implantation range of the stent in the blood vessel is desirably determined in consideration of the foreshortening. In the embodiment, the description will be given about a process of simulating the length of the stent in a case where the stent is implanted into the blood vessel of a patient on the three-dimensional blood vessel image in consideration of the foreshortening.

Herein, the foreshortening in the stent formed by helicoidally braiding the plurality of metal wires is a well-known phenomenon, and thus the description thereof will be omitted. The description below will be given about a flow of implanting the stent to an affected part in treatment using the stent formed by helicoidally braiding the plurality of metal wires, and timing when there may occur the foreshortening in the procedure of implanting the stent.

In the treatment of the cerebral aneurysm using the flow diverter stent, the stent is implanted to the blood vessel of the affected part where the aneurysm exists to suppress a blood stream into the aneurysm so as to promote thrombogenesis, and a film which is not in the surface of the stent is formed to rebuild the blood vessel. Therefore, there is a need to implant the stent to the affected part of a brain blood vessel of the patient.

First, the operator inserts a guide wire up to a distal side (downstream side) of the cerebral aneurysm (the affected part) through the blood vessel from the root of legs of the patient. The guide wire is structured to go in the catheter, and the catheter is inserted up to the distal side (downstream side) of the aneurysm along the inserted guide wire. Thereafter, the guide wire is pulled out. Next, the operator inserts a delivery wire toward the distal side (downstream side) of the aneurysm along the center of the catheter. In the delivery wire, one end of the stent is fixed by a distal coil.

The operator adjusts the position of the delivery wire to pull out the catheter to some degree. At this time, the degree of pulling the catheter is decided by the operator. By pulling out the catheter, the stent fixed to the delivery wire by the distal coil is released from the inside of the catheter into the blood vessel. The released portion of the stent starts to open. Thereafter, the operator unties the fixed distal coil, and pulls out the catheter until the stent is completely released into the blood vessel. Thus, the stent is expanded in the blood vessel and implanted in the blood vessel.

The operator inserts the catheter up to the distal side (downstream side) of the aneurysm again, stores the delivery wire in the catheter, and pulls out the delivery wire and the catheter from the blood vessel. Thus, a work of implanting the stent in the affected part is ended.

In the above flow, one end of the stent is opened at timing when the operator unties the fixed distal coil, and thus the foreshortening starts to occur. Then, the foreshortening keeps going on until the entire stent is released into the blood vessel and implanted.

Figure 2:
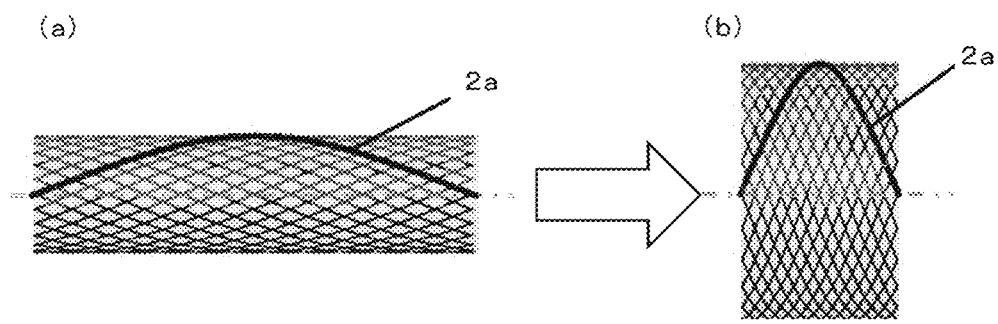
FIG. 2 is a diagram schematically illustrating a stent shape before and after a foreshortening.

FIG. 2 is a diagram schematically illustrating the stent shape before and after the foreshortening occurs. FIG. 2(a) illustrates the stent shape before the foreshortening occurs, and FIG. 2(b) illustrates the stent shape after the foreshortening occurs. As illustrated in FIG. 2, when the stent is implanted in the blood vessel of the patient, and expanded along with a blood vessel diameter of the patient, the diameter of the stent becomes large and the length becomes short due to the foreshortening.

Hereinafter, the description will be given about a process of estimating the stent length implanted in the blood vessel and simulating an implantation start position and an implantation end position of the stent on the three-dimensional blood vessel image in consideration of the foreshortening.

The control device 103 receives a designation of the implantation start position and an implantation direction from a user (for example, the operator) who is an operator of the stent length estimation device 100 on the three-dimensional blood vessel image displayed by the display device 105. For example, the user uses a mouse to click a point corresponding to the implantation start position in the blood vessel on the three-dimensional blood vessel image. Next, the user clicks a position in the implantation direction of the stent from the implantation start position. Therefore, the implantation start position and the implantation direction of the stent can be designated. The control device 103 can specify the first point, which is firstly clicked by the user, as the implantation start position of the stent, and can specify a direction toward the second point secondly clicked by the user from the first point as the implantation direction of the stent.

Figure 3:
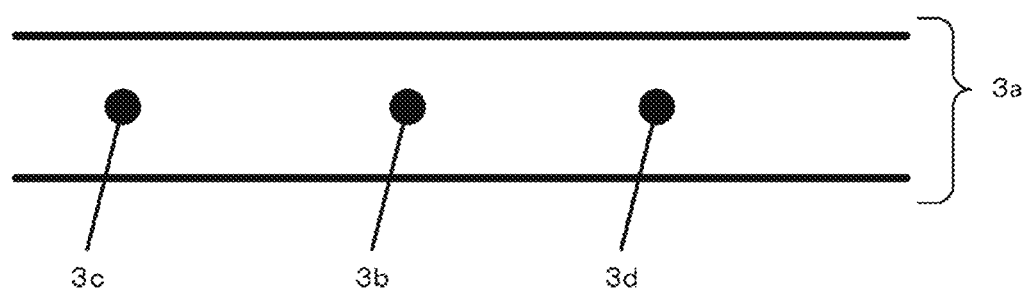
FIG. 3 is a diagram schematically illustrating a method of specifying an implantation start position and an implantation direction of the stent.

FIG. 3 is a diagram schematically illustrating a method of specifying the implantation start position and the implantation direction of the stent. For example, in a case where the user clicks a point 3c after clicking a point 3b on the blood vessel 3a, the control device 103 specifies the point 3b as the implantation start position, and specifies a direction from the point 3b toward the point 3c (that is, a left direction) as the implantation direction. In addition, in a case where the user clicks a point 3d after clicking the point 3b on the blood vessel 3a, the control device 103 specifies the point 3b as the implantation start position, and specifies a direction from the point 3b toward the point 3d (that is, a right direction) as the implantation direction. The control device 103 records information for specifying each of the specified implantation start position and the specified implantation direction of the stent in the buffer memory.

The control device 103 specifies a specification of the stent used in treatment. The specification of the stent required for the process in the embodiment includes a diameter $D_0$ when the stent is expanded, a length $L_0$ when the stent is expanded, the number of wires N of the stent, and a pitch length $p_0$ when the stent of wires forming the stent is expanded. The control device 103 specifies these values as the specification of the stent. The number of wires N of the stent is N=48 for example. In the embodiment, the specification of the stent is registered in the recording device 104 in advance. The control device 103 may read the registered specification and specify the values, or may specify the values by receiving a user's input.

Figure 4:
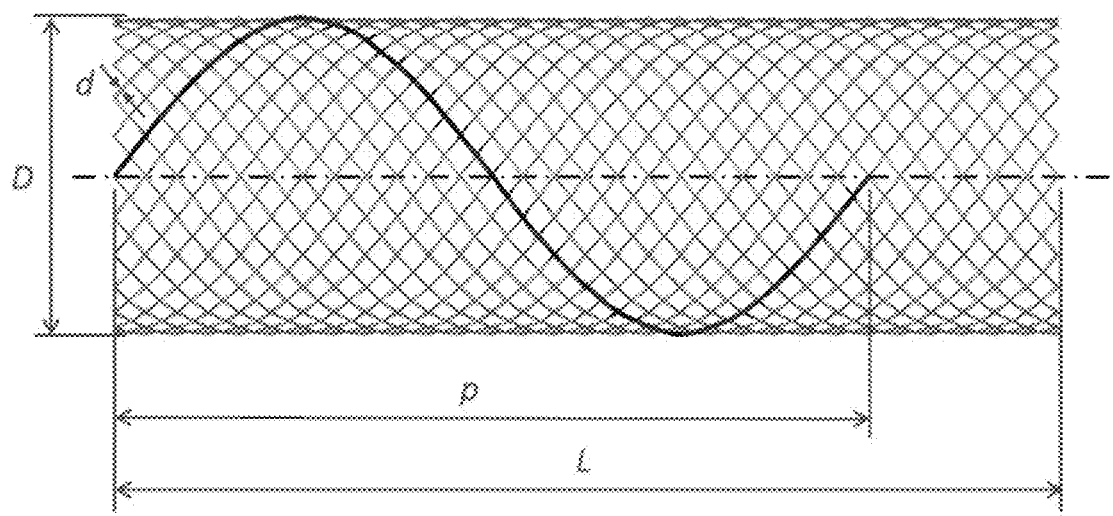
FIG. 4 is a diagram schematically illustrating lengths of portions to define a specification of the stent.

FIG. 4 is a diagram schematically illustrating the diameter D the stent, the length L of the stent, and the pitch length p of the wires of the stent in order to define the specification of the stent. In addition, "d" indicates a diameter of the wire of the stent while not necessary in the embodiment.

The respective parameters $D_0$, $L_0$, and $p_0$ in the case of "when the stent is expanded" in the specification mean values on specification when the stent is expanded in a state where there is no other things surrounding the stent and no external pressure. Therefore, the parameters $D_0$, $L_0$, and $p_0$ defined as the specification are different from the values of D, L, and p in a case where the stent is implanted in an actual blood vessel.

In other words, according to the specification, the length when the stent is expanded is $L_0$, and the pitch length of the wire is $p_0$. However, these values indicate lengths in a case where the stent is expanded over the entire length to be the diameter $D_0$ on specification. With this regard, the stent implanted in the blood vessel is expanded along with the blood vessel diameter of the patient. Therefore, there is a low possibility for the stem to be expanded over the entire length to be the diameter $D_0$ on specification. In this case, the length L when the stent is expanded in the blood vessel becomes a value different from $L_0$, and p becomes a value different from $p_0$.

In the embodiment, taking the above point into consideration, the description will be given about a method of simulating the implantation start position and the implantation end position of the stent by estimating the length of the stent planted in the blood vessel according to the blood vessel diameter of the blood vessel of the patient.

Herein, the description will be given about a method of obtaining a length of the stent after expanded according to the blood vessel diameter of the patient on the basis of the specification of the stent. The length of the stent after expanded according to the blood vessel diameter of the patient can be calculated using the following Expression (5). First, the calculation for deriving Expression (5) will be described.

Figure 5:
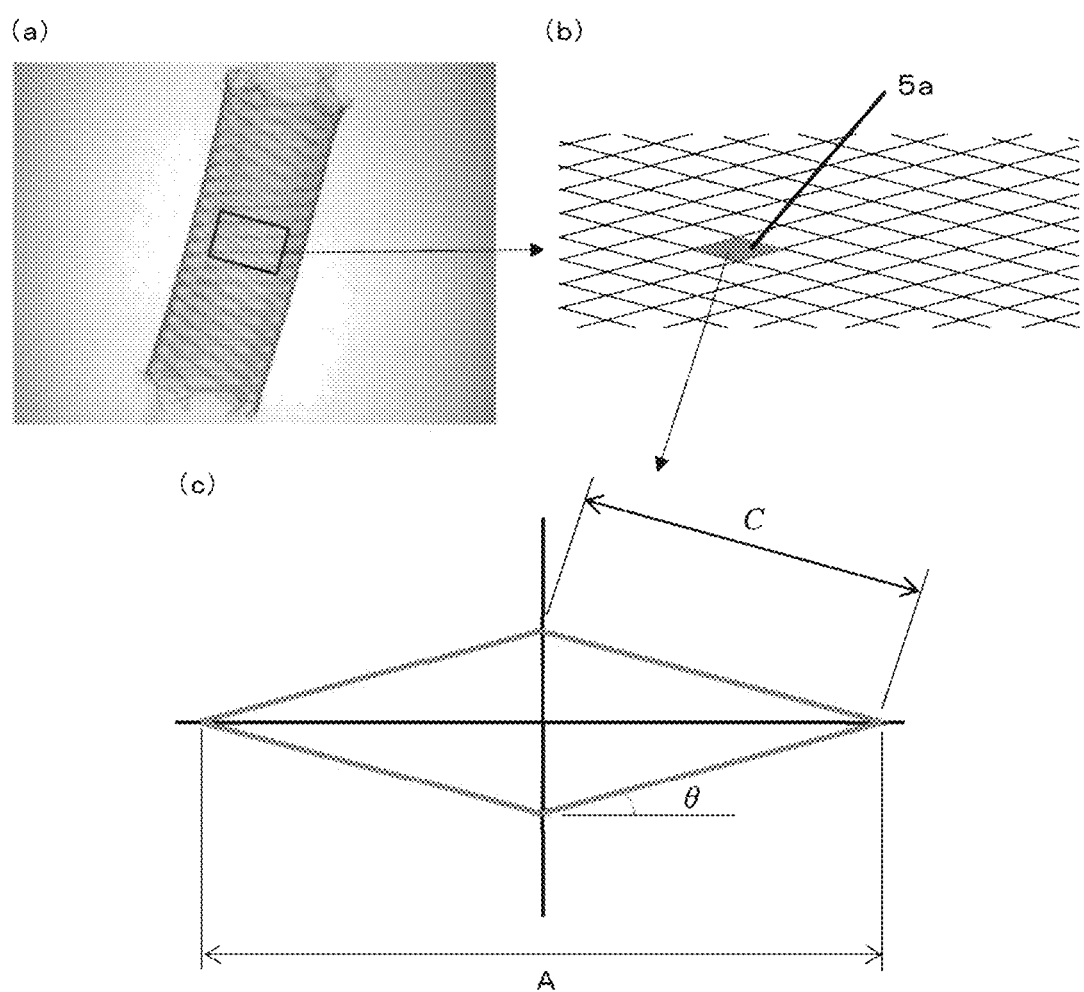
FIG. 5 is a diagram schematically illustrating a small mesh of a stent surface.

FIG. 5(b) schematically illustrates part of the surface of the stent illustrated in FIG. 5(a). A relational Expression (1) is geographically established on one small mesh 5a in FIG. 5(b) on the basis of the specification of the stent as illustrated in FIG. 5(c).

[Mathematical Formula 1]

$$\cos\theta = \frac{A/2}{C} \Leftrightarrow C = \frac{A}{2\cos\theta} = \frac{\pi D}{N\cos\theta} \quad (1)$$

Further, $A=\pi D/(N/2)=2\pi D/N$ is established in Expression (1).

In Expression (1), C is unchanged even when the length of the stent in a lateral direction is changed as illustrated in FIG. 2. Therefore, the following relational Expression (1) is established.

[Mathematical Formula 2]

$$C = \frac{\pi D_0}{N\cos\theta_0} = \frac{\pi D}{N\cos\theta} \Leftrightarrow \cos\theta = \frac{D}{D_0}\cos\theta_0 \quad (2)$$

Further, since the number of wires forming the stent is unchanged even when the length of the stent in the lateral direction is changed as illustrated in FIG. 2, the following relational Expression (3) is established. Further, it can be seen in FIG. 2 that a wire 2a forms a half circle of the stent in both of FIGS. 2(a) and 2(b).

[Mathematical Formula 3]

$$\frac{L_0}{p_0} = \frac{L}{p} \Leftrightarrow L = \frac{L_0}{p_0}\pi D\tan\theta \quad (3)$$

When Expression (2) is substituted to Expression (3), the following Expression (4) is obtained. With the following Expression (4), the length L in a case where the stent is opened to be the diameter D in the blood vessel of the patient can be calculated. In other words, according to the following Expression (4), the length L of the expanded stent in a case where the blood vessel diameter of the patient is D over the entire length can be calculated.

[Mathematical Formula 4]

$$L = \frac{\pi L_0}{p_0 \cos\theta_0} \sqrt{D_0^2 - D^2(\cos\theta)^2} \quad (4)$$

As described above, since the stent implanted in the blood vessel is expanded along with the blood vessel diameter, there is a less possibility that the stent is opened with the same diameter D over the entire length. Therefore, taking the above point into consideration, the embodiment will be described about a method of obtaining the length of the implanted stent with a high accuracy.

Figure 6:
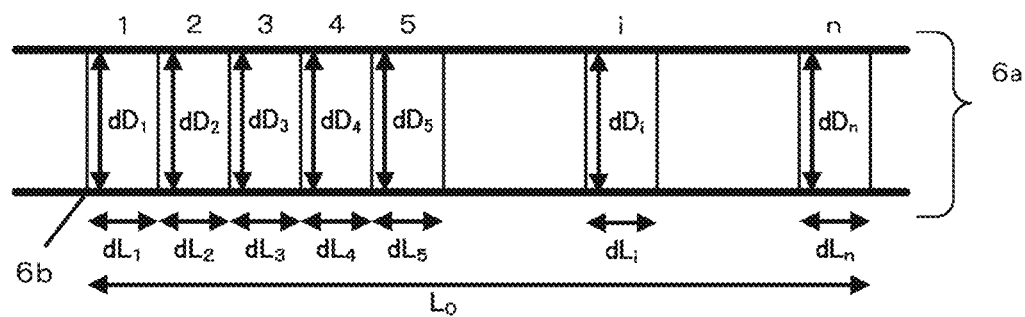
FIG. 6 is a diagram schematically illustrating a division example of a blood vessel region in a three-dimensional blood vessel image.

In the embodiment, as illustrated in FIG. 6, the control device 103 divides a blood vessel region 6a (a section from an implantation start position 6b to the length $L_0$) on the three-dimensional blood vessel image into "n" (fine sections) to obtain then fine sections. The control device 103 calculates a length dLi ("i" is an integer of 1 to n) of the implanted stent in an i-th fine section by the following Expression (5) using an average value dDi ("i" is an integer of 1 to n) of the blood vessel diameter in each fine section.

[Mathematical Formula 5]

$$dL_i = \frac{\pi \frac{L_0}{n}}{p_0 \cos\theta_0} \sqrt{D_0^2 - dD_i^2(\cos\theta)^2} \quad (5)$$

The control device 103 calculates a length LS of the implanted stent by summing up the values from dL1 to dLn calculated by Expression (5). The number ("n") of divisions in Expression (5) is set in advance. While the number is not particularly limited, the calculation accuracy of the length LS of the implanted stent is improved as "n" is set to be large to increase the number of divisions.

Further, since FIG. 6 schematically illustrates the blood vessel 6a, the blood vessel is illustrated as linear and the same diameter over the entire length. In practice, since the blood vessel on the three-dimensional blood vessel image is divided into fine sections, the blood vessels have various shapes, and even the blood vessel diameters are different depending on places. Therefore, the average value dDi of the blood vessel diameters calculated in the respective sections is different at every section. In addition, a method of calculating the average value dDi of the blood vessel diameters in the respective fine sections is not particularly limited. For example, the control device 103 extracts a region within the threshold range of the pixel value to extract the blood vessel region from the three-dimensional blood vessel image colored with the white/black gradation as a three-dimensional blood vessel region. The diameters of the three-dimensional blood vessel regions in a plurality of places in the fine section may be specified, and averaged.

The control device 103 displays information to specify the implantation range of the stent on the three-dimensional blood vessel image on the basis of the designated implantation start position, the designated implantation direction, and the calculated length LS of the implanted stent. For example, the control device 103 displays a mark indicating the implantation start position at the implantation start position on the blood vessel of the three-dimensional blood vessel image, and displays a mark indicating the implantation end position at a position shifted by the length LS in the implantation direction from the implantation start position. With this configuration, the user can visually recognize the implantation start position and the implantation end position on the three-dimensional blood vessel image, and thus can ascertain the implantation range of the stent in advance.

Further, a method of specifying a position shifted by the length LS in the implantation direction from the implantation start position is not particularly limited. For example, the control device 103 may specify the length as follows. The control device 103 creates voxel data by filling the inner portion of the three-dimensional blood vessel region (that is, the empty inner space of the blood vessel) with voxels. The voxel data is removed from the outer side, and the remaining voxels in the center portion are linked to create a center line of the blood vessel. Then, the control device 103 may specify a position of the length LS in the implantation direction from the implantation start position on the center line of the blood vessel as the implantation start position.

Figure 7:
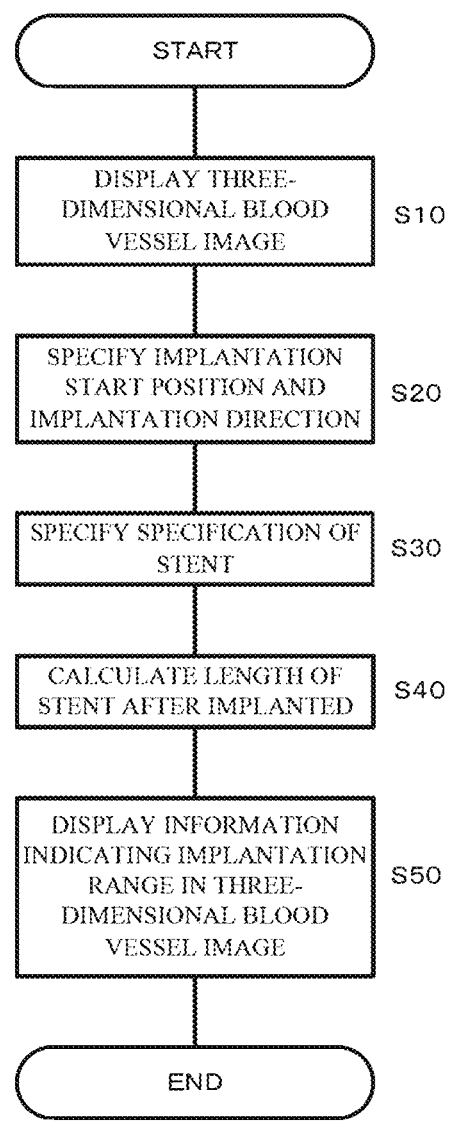
FIG. 7 is a flowchart illustrating a processing flow performed by the stent length estimation device 100 in the embodiment.

FIG. 7 is a flowchart illustrating a processing flow performed by the stent length estimation device 100 in the embodiment. The process illustrated in FIG. 7 is performed as a program which is activated by the control device 103 when the operator of the stent length estimation device 100 commands the execution of the program. Further, in the process illustrated in FIG. 7, the three-dimensional blood vessel data generated in advance on the basis of the captured image of the affected part of the patient is assumed to be recorded in the recording device 104.

In step S10, the control device 103 reads out the three-dimensional blood vessel data from the recording device 104, and displays the data in the display device 105. Then, the procedure proceeds to step S20.

In step S20, the control device 103 detects a user's operation as described above, and specifies the implantation start position and the implantation direction of the stent in the blood vessel on the three-dimensional blood vessel image. Then, the procedure proceeds to step S30.

In step S30, the control device 103 specifies, as described above, the diameter $D_0$ when the stent is expanded, the length $L_0$ when the stent is expanded, the number of wires N of the stent, and the pitch length $p_0$ when the stent of the wires forming the stent is expanded as the specification of the stent. Then, the procedure proceeds to step S40.

In step S40, the control device 103 calculates, as described above, the length L of the implanted stent for every fine section using Expression (5), and sums up the lengths to calculate the length LS of the implanted stent. Then, the procedure proceeds to step S50.

In step S50, the control device 103 displays information to specify the implantation range of the stent on the three-dimensional blood vessel image on the basis of the implantation start position, the implantation direction, and the calculated length LS of the implanted stent as described above. Then, the process ends.

According to the embodiment described above, the following operational effects can be achieved.

(1) The control device 103 receives a designation of the implantation start position of the aneurysm treatment stent which is formed by helicoidally braiding the plurality of metal wires from the user, and specifies the implantation start position of the stent on the three-dimensional blood vessel image which represents a three-dimensional shape of the blood vessel. The control device 103 receives a designation of the implantation direction of the stent from the user, and specifies the implantation direction of the stent on the three-dimensional blood vessel image. The control device 103 specifies the diameter Do of the stent after expanded, the length $L_0$ of the stent after expanded, the number of wires N of the stent, and the pitch length $p_0$ of the wires of the stent after expanded as the specification of the stent. The control device 103 is configured to calculate the length LS of the stent which is expanded along with the blood vessel diameter and is implanted on the basis of the specified specification of the stent and the blood vessel diameter of the blood vessel in the implantation direction from the implantation start position. With this configuration, it is possible to estimate a length of the implanted stent which is expanded according to the blood vessel diameter of the patient in consideration of the foreshortening in the stent formed by helicoidally braiding the plurality of metal wires.

(2) The control device 103 is configured to display information indicating the implantation start position of the stent and information indicating the implantation end position in the three-dimensional blood vessel image on the basis of the implantation start position of the stent, the implantation direction of the stent, and the calculated implanted stent length LS. With this configuration, the user can confirm an estimation result of the implantation range of the stent on the three-dimensional blood vessel image.

(3) The control device 103 is configured to divide the blood vessel into the fine sections on the three-dimensional blood vessel image, calculate the length for every fine section after the stent is implanted, and calculate the implanted stent length by adding the lengths. With this configuration, it is possible to calculate the length of the implanted stent with a high accuracy even when the blood vessel is not even in diameter.

Modifications

Further, the stent length estimation device 100 of the above-described embodiment may be modified as follows.

(1) In the above-described embodiment, the description has been given about the process in which the control device 103 estimates the length of the implanted stent, taking an example of a case where the flow diverter stent formed by helicoidally braiding 48 (N=48) metal wires is implanted in the blood vessel. However, the stent to which the invention is applied is not limited to the configuration of N=48 and to the flow diverter stent as long as the stent is formed by helicoidally braiding the plurality of metal wires.

(2) In the above-described embodiment, the description has been given about an example using a personal computer configured as illustrated in FIG. 1 as the stent length estimation device 100. However, the configuration of the stent length estimation device 100 is not limited to that illustrated in FIG. 1, and other configurations may be applied as long as the device can perform the process of the above-described embodiment. For example, the stent length estimation device 100 may record various types of data in an external storage device which is connected through a communication line or a wired cable without the recording device 104. In addition, the stent length estimation device 100 may display information in an external monitor which is connected through the connection interface 102 without the display device 105.

Further, the invention is not limited to any one of the configurations of the above-described embodiment as long as the characteristic functions of the invention are not degraded. In addition, the above-described embodiment and a plurality of modifications may be combined.

Priority is claimed on Japanese Patent Application No. 2016-26784 filed on Feb. 16, 2016, the content of which is incorporated herein by reference.

REFERENCE SIGNS LIST 100 stent length estimation device
101 operation member
102 connection interface
103 control device
104 recording device
105 display device

The invention claimed is:

1. A stent length estimation device, comprising:
an implantation start position specifying means for receiving, from a user, a designation of an implantation start position of an aneurysm treatment stent which is formed by helicoidally braiding a plurality of metal wires, and specifying the implantation start position of the stent on a three-dimensional blood vessel image which represents a three-dimensional shape of a blood vessel;
an implantation direction specifying means for receiving, from the user, a designation of a position located in a desired implantation direction of the stent among positions located in a plurality of implantation directions of the stent from the implantation start position, and specifying the implantation direction of the stent on the three-dimensional blood vessel image;
a stent specification specifying means for specifying a diameter of the stent after expanded, a length of the stent after expanded, the number of wires of the stent, and a pitch length of the wires of the stent after expanded as a specification of the stent; and
an implanted stent length calculating means for calculating a length of the stent after the stent is implanted in a blood vessel, expanded along with a blood vessel diameter, and shortened in the implantation direction, on the basis of the specification of the stent specified by the stent specification specifying means and the blood vessel diameter of the blood vessel in the implantation direction specified by the implantation direction specifying means from the implantation start position specified by the implantation start position specifying means.

2. The stent length estimation device according to claim 1, further comprising:
a display means for displaying information indicating the implantation start position of the stent and information indicating an implantation end position in the three-dimensional blood vessel image on the basis of the implantation start position of the stent which is specified by the implantation start position specifying means, the implantation direction of the stent which is specified by the implantation direction specifying means, and an implanted stent length which is calculated by the implanted stent length calculating means.

3. The stent length estimation device according to claim 1,
wherein the implanted stent length calculating means divide the blood vessel into multiple sections on the three-dimensional blood vessel image, calculates a length of the implanted stent for every section, and calculates the implanted stent length by summing up the lengths.

4. A non-transitory computer-readable storage medium storing a stent length estimation program for causing a computer to perform:
an implantation start position specifying procedure for receiving, from a user, a designation of an implantation start position of an aneurysm treatment stent which is formed by helicoidally braiding a plurality of metal wires and specifying the implantation start position of the stent on a three-dimensional blood vessel image which represents a three-dimensional shape of a blood vessel;
an implantation direction specifying procedure for receiving, from the user, a designation of a position located in a desired implantation direction of the stent among positions located in a plurality of implantation directions of the stent from the implantation start position, and specifying the implantation direction of the stent on the three-dimensional blood vessel image;
a stent specification specifying procedure for specifying a diameter of the stent after expanded, a length of the stent after expanded, the number of wires of the stent, and a pitch length of the wires of the stent after expanded as a specification of the stent; and
an implanted stent length calculating procedure for calculating a length of the stent after the stent is implanted in a blood vessel, expanded along with the blood vessel diameter, and shortened in the implantation direction, on the basis of the specification of the stent which is specified by the stent specification specifying procedure and a blood vessel diameter of the blood vessel in the implantation direction which is specified by the implantation direction specifying procedure from the implantation start position specified by the implantation start position specifying procedure.

5. The non-transitory computer-readable storage medium storing the stent length estimation program according to claim 4, further comprising:
a display procedure for displaying information indicating the implantation start position of the stent and information indicating an implantation end position in the three-dimensional blood vessel image on the basis of the implantation start position of the stent which is specified by the implantation start position specifying procedure, the implantation direction of the stent which is specified by the implantation direction specifying procedure, and the implanted stent length which is calculated by the implanted stent length calculating procedure.

6. The non-transitory computer-readable storage medium storing the stent length estimation program according to claim 4,
wherein, the implanted stent length calculating procedure divides the blood vessel into multiple sections on the three-dimensional blood vessel image, calculates a length of the implanted stent for every section, and calculates the implanted stent length by summing up the lengths.

7. A method of estimating a length of a stent, comprising:
receiving, by an implantation start position specifying means from a user, a designation of an implantation start position of an aneurysm treatment stent which is formed by helicoidally braiding a plurality of metal wires and specifying the implantation start position of the stent on a three-dimensional blood vessel image which represents a three-dimensional shape of a blood vessel;
receiving, by an implantation direction specifying means from the user, a designation of a position located in a desired implantation direction of the stent among positions located in a plurality of implantation directions of the stent from the implantation start position, and specifying the implantation direction of the stent on the three-dimensional blood vessel image;
specifying, by a stent specification specifying means, a diameter of the stent after expanded, a length of the stent after expanded, the number of wires of the stent, and a pitch length of the wires of the stent after expanded as a specification of the stent; and
calculating, by an implanted stent length calculating means, a length of the stent after the stent is implanted in a blood vessel, expanded along with the blood vessel diameter, and shortened in the implantation direction, on the basis of the specification of the stent which is specified by the stent specification specifying means and a blood vessel diameter of the blood vessel in the implantation direction which is specified by the implantation direction specifying means from the implantation start position specified by the implantation start position specifying means.

8. The method of estimating the length of the stent according to claim 7, further comprising:
displaying, by a display means, information indicating the implantation start position of the stent and information indicating an implantation end position in the three-dimensional blood vessel image on the basis of the implantation start position of the stent which is specified by the implantation start position specifying means, the implantation direction of the stent which is specified by the implantation direction specifying means, and the implanted stent length which is calculated by the implanted stent length calculating means.

9. The method of estimating the length of the stent according to claim 7,
wherein the implanted stent length calculating means divides the blood vessel into multiple sections on the three-dimensional blood vessel image, calculates a length of the stent after implanted for every section, and calculates the implanted stent length by summing up the lengths.

* * * * *